United States Patent [19]

Wissner et al.

[11] Patent Number: 5,124,147
[45] Date of Patent: Jun. 23, 1992

[54] METHOD FOR THE TREATMENT OF ENDOTOXIC SHOCK IN A MAMMAL

[75] Inventors: Allan Wissner, Ardsley; Suresh S. Kerwar, Ossining; Constance Kohler, Old Tappan, all of N.Y.

[73] Assignee: American Cyanamid Company, Stamford, Conn.

[21] Appl. No.: 482,141

[22] Filed: Feb. 16, 1990

Related U.S. Application Data

[63] Continuation-in-part of Ser. No. 286,201, Dec. 19, 1988, abandoned.

[51] Int. Cl.⁵ .......................................... A61K 39/395
[52] U.S. Cl. .................................................. 424/85.8
[58] Field of Search ....................................... 424/85.8

[56] References Cited

PUBLICATIONS

Tracey et al. Science vol. 234, Oct. 24, (1986) pp. 470–474.
Beutler et al. Science vol. 229 (1985) Aug. 30, pp. 869–871.
Terashita et al. Europ. J. of Pharmacology (1985) vol. 109, pp. 257–261.

Primary Examiner—F. T. Moezie
Assistant Examiner—Choon Park Koh
Attorney, Agent, or Firm—H. G. Jackson

[57] ABSTRACT

The invention is a method of treating endotoxic shock in a mammal which comprises administering to the mammal a therapeutically effective amount of an antagonist to Platelet Activating Factor in combination with a therapeutically effective amount of one or more monoclonal or polyclonal antibodies directed toward either Tumor Necrosis Factor $\alpha$, Interleukin-1$\beta$, Gamma Interferon, or bacterial cell wall lipopolysaccharides.

7 Claims, No Drawings

METHOD FOR THE TREATMENT OF ENDOTOXIC SHOCK IN A MAMMAL

BRIEF SUMMARY OF THE INVENTION

This invention relates to a method of treatment of endotoxic shock in mammals which is useful to retard and/or inhibit the development of clinical lesions associated with endotoxic shock. More particularly, it relates to therapeutic compositions containing a combination of a Platelet Activating Factor antagonist and a monoclonal or polyclonal antibody directed to either Tumor Necrosis Factor $\alpha$, interleukin-1$\beta$, gamma interferon or bacterial cell wall lipopolysaccharide/s. The invention includes a new method for the treatment of endotoxic shock in mammals therewith.

DETAILED DESCRIPTION OF THE INVENTION

Platelet Activating Factor (PAF) is a potent mediator of inflammation in mammals and it is synthesized by a variety of cells including macrophages, neutrophils, endothelial cells and platelets (Cammussi, G. 1986, Kidney Int. 29, 469). When injected into mammals, PAF induces hemodynamic and hematological changes including hypotension, platelet aggregation, neutropenia, disseminated intravascular coagulation, increases in vascular permeability, bronchoconstriction, tissue injury (hypoxia and necrosis) and eventually death (reviewed by Cammussi, G. Kidney Int. 29, 469, 1986). In recent years, it has been postulated that PAF is the mediator of tissue injury in mammals undergoing endotoxic shock due to bacterial sepsis (Terashita, Z., Y. Imura, K. Nishikawa and S. Sumida 1985, Eur. J. Pharmacol. 109:257-261; Doebber, T. W., M. S. Wu, J. C. Robbins, B. M. Choy, M. N. Chang and T. Y. Shen 1985, Biochem. Biophys. Res. Comm 127:799-808; Inarrea, P., Gomez-Cambronero, J. Pascual, M. del Carmen Ponte, L. Hernando and M. Sanchez-Crespo. 1985, Immunopharmacology, 9:45-52). These studies, in mammals, have shown that PAF is produced in large amounts when the mammal has been treated with endotoxin. In addition, mammals undergoing endotoxic shock exhibit all of the clinical symptoms associated with the administration of PAF.

Studies (Tracey, K. J., B. Beutler, S. F. Lowry, J. Merryweather, S. Wolpe, I. W. Milsark, R. J. Hairi, T. J. Fahey, A. Zentalla, J. D. Albert and A. Cerami 1986, Science (Wash., D.C. 234;47-473) have shown that the clinical symptoms associated with endotoxic shock or with PAF can be reproduced in mammals by the administration of the macrophage cytokine, Tumor Necrosis Factor $\alpha$ (TNF$\alpha$; also known as cachectin). Since macrophages can be activated in vitro and in vivo, to synthesize and secrete TNF$\alpha$ (Carswell, E. A., L. J. Old, R. L. Kassel, S. Green, D. Fiore and B. Williamson 1975, Proc. Natl. Acad. Sci. USA 72;:3666-3671), it has been suggested that TNF$\alpha$ may be one of the mediators synthesized after endotoxin shock. Evidence supporting this claim is derived from the studies of Beutler et al. (Beutler, B., I. W. Milsark and A. C. Cerami 1985, Science (Wash. D.C.) 229;869-872). These studies have shown that if mice are pretreated with polyclonal antisera directed against TNF$\alpha$ (antiTNF$\alpha$), they were protected from the lethal effects of endotoxin. However, if antiTNF$\alpha$ was administered at the time of endotoxin treatment or if antiTNF$\alpha$ was administered after endotoxin treatment, no significant protection was detected. Thus, the time of administration of antiTNF$\alpha$ was critical in the protection against endotoxin induced lethality.

Recent studies by Camussi et al. (Camussi, G., F. Bussolino, G. Salvidio and C. Baglioni 1987, J. Exp. Med. 166, 1390-1404) have shown that when TNF$\alpha$ is added to cultures of rat peritoneal macrophages, neutrophils or human endothelial cells, large amounts of PAF are synthesized and released. These observations indicate that the clinical symptoms associated with the administration of TNF$\alpha$ to mammals are due in part to PAF that is synthesized by a variety of cells when exposed to TNF$\alpha$.

Since endotoxin shock is initiated by the cell wall lipopolysaccharide (LPS) a monoclonal or a polyclonal antibody directed against LPS in combination with a PAF antagonist can also be a desired form of treatment for endotoxic shock in mammals.

Since macrophages can be activated by gamma interferon (A. G. Morris, Interferons, Immunology 1988 Supplement 1,43-45), a monoclonal or polyclonal antibody directed to human gamma interferon in combination with a PAF antagonist can also be a desired form of treatment for endotoxic shock in mammals.

Another cytokine that is synthesized and released by macrophages exposed to endotoxin is interleukin-1$\beta$ (IL-1$\beta$). Studies conducted by Okusawa et al. (S. Okusawa, J. A. Gelfand, T. Ikejima, R. J. Connolly and C. A. Dinarello, 1988, Clin. Invest. 81, 1162-1172) have shown that the administration of 1L-1$\beta$ to mammals induces a shock like state (hemodynamic and hematological changes) that is similar to that seen when TNF$\alpha$ is administered. When 1L-1$\beta$ was combined with TNF$\alpha$, the shock syndrome in rabbits was of a greater intensity than if either agent was used alone. Thus, it is likely that 1L-1$\beta$ is an additional mediator that can induce the synthesis and release of PAF by a variety of cells.

Thus, endotoxin shock due to bacterial sepsis involves the synthesis and release of 1L-1$\beta$ and TNF$\alpha$ by macrophages. The released 1L-1$\beta$ and TNF$\alpha$ can interact with a variety of cells such as macrophages, endothelial cells, neutrophils and platelets to stimulate the synthesis and release of PAF. The released PAF induces hemodynamic and hematological changes, causes tissue damage (hypoxia), increased vascular permeability and organ failure. Due to these induced changes in the mammal, PAF is lethal.

Concurrently, with the realization that PAF is an important mediator of the clinical effects in mammals undergoing endotoxic shock, a number structurally different antagonists of PAF have been developed. References to some of these antagonists are listed hereinbelow.

Terashita, z., et. al., Life Sci. 32, 1975 (1983).
Miyamoto, T., et. al., In Advances in Prostaglandin, Thromboxane and
Leukotriene Research, Vol 15 pp. 719-720, Raven Press, New York.
Barner, R., et. al., Eur. patent 147768 (10.07.1985), 41 pp.
Burri, K., et. al., Prostaglandins 30, 691 (1985).
Handley, D. A., et al., Proceedings of the first Sandoz Research Symposium.
"New Horizons in Platelet-activating Factor", pp 335-342, J. Wiley, London, 1987.
VanValen, R. G., et al., ibid., pp 123-130.

Winslow, C. M., et. al., ibid., pp 152-164.
Lee, M. L., et. al., ibid.
Handley, D. A., et. al., Immunopharmacology 11, 175-182 (1986).
Winslow, C. M. et. al., Prostaglandins 30 m 697 (1985). Steiner, M., et. al., Biochem. Biophys. Res. Commun. 133,851 (1985).
Wichrowski, B., et. al., In Sixth Int's Conf. on Prostaglandins and Related Compounds, Florence, Italy, Jun. 3-6, 1986, p. 309.
Lee, M. L., et. al., Prostaglandins 30, 690 (1985).
Jaeggi, C., et. al., Eur. patent appl. EP 178,261 (Apr. 16, 1986), U.S. Appln. 659,249 (Oct. 10, 1984).
Stenzel, H., et. al., In Third Int'l. Symposium, Davos, Switzerland, Sep. 7-9, 1986, p 50.
Braquet, P., In Adv. in Prostaglandin, Thromboxane and Leukotriene Res., Vol. 16, pp. 179-198, Raven Press, New York, 1986.
Dupont, L., et. al., Actz. Crystallog. C42:1759 (1986). Braquet, P., GB Patent 84/18424 (Jul. 19, 1984), Belg. BE 901,915.
Braquet, P., et. al., Blood Vessels 16, 559 (1985).
Korth, R., et. al., Eur. J. Pharmacol., in press, 1987.
Kuster, L. J., et. al., Thromb. Res. 43:425 (1986).
Nunez, D., et. al., Eur. J. Pharmacol. 123:197 (1986).
Baroggi, N., et. al., Agents Actions (suppl.) 20, 87 (1986).
Simon, A. F., et. al., Thromb. Res. 1987.
Chung, K. F., et. al., Lancet 2, 248 (1987).
Rao, C.B.S.: Chemistry of LIgnans, Anhdra Univ. Press, India, p. 377, 1978.
Godfroid, J. J., et. al., J. Med. Chem. 30:792-797, 1987.
Comez-Cambrenero, J., et. al., Biochem. Biophys. Acta 845:511-515, 1985.
Hwang, S. B., et. al., J. Biol. Chem. 261:13720 (1986).
Ponpipom, M. M., et. al., J. Med. Chem. 30, 136 (1987).
Shen, T. Y., et. al., Proc. Natl. Acad. Sci. USA 82:672 (1985).
Hwang, S. B., et. al., Lab. Invest. 52:617 (1985).
Doebber, T. W., et. al., Biochem. Biophys. Res. Commun. 29:799 (1985).
Biftu, T., et. al., Eur. Patent Appln. EP 154887 (18.091985), 34 pp.
Biftu, T., et. al., J. Med. Chem. 29:1917 (1986).
Braquet, P., et. al., Trends Pharmacol. Sci. 7:397 (1986).
Hwang, S. B., et. al., J. Biol. Chem. 260:15639 (1985).
Shen, T. Y., et. al., Second World Conf. on Inflammation, Monte Carlo, 1986.
Shen, T. Y., et. al., Second Int'l. Conf. on Platelat-activating Factor and Structurally related Alkyl Ether Lipids, Gatlinburgh, TN, Oct. 1986, p. 34.
Setchell, K. D., et. al., Nature (Lond) 287:740 (1980).
Stitch, S. R., et. al., Nature (Lond) 287:738 (1980)
Okamoto, M., et. al., J. Antiobiot. (Tokyo) 39:198 (1986).
Okamoto, M., et. al., Chem. Pharm. Bull. (Tokyo) 34:345 (1986).
Okamoto, M., et. al., ibid, 34:340 (1986).
Lefort, J., et. al., Eur. J. Pharmacol., in press, 1987.
Sedivy, P., et. al., Adv. in Inflammation Res., vol. 10 pp. 171-173, Raven Press, New York, 1985.
Sedivy, P., et. al., Prostaglandins 30:688 (1985).
Cavero, L., et. al., Br. J. Pharmacol. 90:116 (1987).
Hwang, S. B., et. al., Thromb. Res. 34:519 (1984)
Kornecki, E., et. al., Science (Wash., D.C.) 226:1454 (1985).
Casais-Stenzel, J., et. al., Ger. Offen. DE 3435974 (10.041986), 22 pp.
Casals-Stenzel, J., et. al., Ger. Offen. DE 3435973 (10.04.1986), 26 pp.
Casals-Stenzel, J., et. al., Ger. Offen. DE 3435972A1 (10.04.1986), 24 pp.
Weber, K. H. et. al., Second Int'l. Conf. on Platelet Activating Factor and Structurally Related Alkyl Ether Lipids, Gatlinburg, TN, Oc. 1986, p. 29.
Tuffin, D. P., et. al., Prostaglandins 30:702 (1985).
Hwang, M. N., et. al., Eur. J. Pharmacol., in press, 1987.
Hadvary, P., et. al., Helv. Chimica Acta 69, 1862 (1986).
Kagari, F., et. al., Chem. Pharm. Bull. 35, 647 (1987).
Grue-Sorensen, G., et. al., submitted J. Org. Chem., 1987.
Bittman, R., et. al., J. Lipid Res., 28, 733 (1987).
Shimazaki, N., et. al., J. Med. Chem. 30, 1706 (1987).
O'Flaherty, J. T., et. al., Biochem. and Biophys. Res. Commun. 147, 18 (1987).
Bitterman, H., et. al., Meth and Find Exptl. Clin. Pharmacol. 9, 341 (1987).
Hwang, S., et. al., Eur. J. Pharmacol. 141, 269 (1987).

In addition to the references given above, our copending applications U.S. Ser. No. 177,299 and U.S. Pat. No. 4,983,592 (1991), disclose additional PAF antagonists.

Our invention relates to the unexpected discovery that when a PAF antagonist is administered in combination with a monoclonal or polyclonal antibody directed toward either Tumor Necrosis Factor $\alpha$, Interleukin-1$\beta$, gamma interferon, or bacterial cell wall lipopolysaccharides, the animals can be protected from the effects of endotoxin in a manner better than if the PAF antagonist or the antibody are administered alone; this combination therapy represents a new method for the treatment of endotoxic shock in mammals.

Antibody directed toward Tumor Necrosis Factor $\alpha$ can be obtained from Endogen Inc., 451 D Street, Boston, MA 02210. Antibody directed toward Interleukin-1$\beta$ can be obtained from Genzyme, 75 Kneeland St., Boston, MA 02114. Antibody directed toward gamma interferon can be obtain from Alpha Therapeutic Corp., 5555 Valley Road, Los Angeles, CA 90032. Antibody directed toward bacterial cell wall lipopolysaccharides can be obtained from Oxoid Ltd., Wade Road, Basingstoke, Hampshire, RG 24, OPN, England.

The PAF antagonists used to implement the present invention may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these antagonists may be incorporated with excipients and used in the form of tablets, capsules, elixirs, suspensions, syrups and the like. Such compositions and preparations should contain at least 0.1% of active compound. The percentage of the compound in these compositions may, of course, be varied and may conveniently be between about 2% to about 60% of the weight of the unit. The amount of active compound in such therapeutically useful compositions is such that a suitable dosage will be obtained. Preferred compositions according to this invention are prepared so that an oral dosage unit contains between about 1 and 500 mg of active compound.

The tablets, capsules and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When the dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to active ingredient, sucrose as a sweetening agent, methyl and propylparabens as preservatives, a dye and flavoring such as cherry or orange flavor.

These PAF antagonists may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms of PAF antagonists suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The PAF antagonists of this invention may also be administered directly to the airways in the form of an aerosol.

The monoclonal or polyclonal antibodies directed towards Tumor Necrosis Factor $\alpha$ (also known as Cachectin), Interleukin-1$\beta$, Gamma Interferon, and bacterial cell wall lipopolysaccharides which are needed to implement this invention and are best administered parenterally in a dosage range of 2 to 500 mg/kg.

Solutions or suspensions of these antibody compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms of the antibodies suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, saline, water, ethanol, polyol (e.g. glycerol, propylene glycol and liquid polyethylene glycol), suitable mixtures thereof, and vegetable oils.

The PAF antagonists and antibodies may be administered in the same vehicle or different vehicles. The PAF antagonists and antibodies may be administered at the same time or at different times during the course of therapy.

The invention will be further described by the following examples.

EXAMPLE 1

Balb/c mice (male, 20 g) were obtained from Charles River Laboratories, Wilmington, Mass. They were housed in groups of 5 in individual cages and fed ad libitum. E. coli endotoxin was obtained from Sigma Chemical Co., St. Louis, MO. The endotoxin was dissolved in Phosphate buffered saline (GIBCO) and administered to mice intravenously at a dose of 50 mg/kg. Fifteen to twenty minutes after the administration of endotoxin, the mice were divided into several groups. One group received intravenous saline (Control). The second group received 3-[[3-[[hydroxy[2-methoxy-3-(tetradecyloxy)phenoxy]-phosphinyl]oxy]phenyl]methyl]-5-methyl-thiazolium, hydroxide, inner salt (PAF antagonist) intravenously at a dose of 20 mg/kg (Compound suspended in phosphate buffered saline and sonicated for approximately 15 seconds to provide a flocculent or cloudy solution). The third group received a monoclonal antibody directed against murine TNF$\alpha$ administered intravenously at a dose of 25 mg/kg. The fourth group received intravenously 3-[[3-[[hydroxy[2-methoxy-3-(tetradecyloxy)phenoxy]-phosphinyl]oxy]-phenyl]methyl]-5-methyl-thiazolium, hydroxide, inner salt (20 mg/kg) and the monoclonal antibody directed against murine TNF$\alpha$ (25 mg/kg). The monoclonal antibody used in these studies was provided by Dr. Robert Schreiber, Department of Pathology, Washington University School of Medicine, St. Louis, MO and Cell-Tech, Great Britain. The mice were monitored for survival for up to 72 hours post endotoxin treatment. The results of these studies are shown in Table I.

Control mice that had received saline died within 24 hours after endotoxin challenge. Consistent with the observations of Beutler et al. (see reference above), mice that had received endotoxin followed by antiTNF$\alpha$ (antiTNF$\alpha$ administered 15 to 20 minutes after endotoxin) were not protected. By 72 hours, all of the mice had succumbed to the lethal effects of endotoxin. Mice treated with 3-[[3-[[hydroxy[2-methoxy-3-(tetradecyloxy)phenoxy]-phosphinyl]oxy]phenyl]methyl]-5-methyl-thiazolium, hydroxide, inner salt were also not protected from lethality induced by endotoxin. However, mice that had received both 3-[[3-[[hydroxy[2-methoxy-3-(tetradecyloxy)phenoxy]-phosphinyl]oxy]-phenyl]methyl]-5-methyl-thiazolium, hydroxide, inner salt and antiTNF$\alpha$ were completely protected from endotoxin induced lethality. No mortality was observed in this group at 24 hours or 72 hours post endotoxin treatment. They appeared healthy and for up to 13 days post endotoxin treatment. The experiment was terminated at this time.

EXAMPLE 2

Several Balb/c mice were treated intravenously with either 3-[[3-[[hydroxy[2-methoxy-3-(tetradecyloxy)-phenoxy]phosphinyl]oxy]phenyl]methyl]5-methyl-thiazolium, hydroxide, inner salt (20 mg/kg) or with saline. After two hours, all of these mice were treated intravenously with endotoxin at a dose of 50 mg/kg. One hour after endotoxin treatment, the mice were divided into several groups. Some mice that had received saline followed by endotoxin were treated intravenously with various doses of antiTNFα (doses ranging from 2.5 to 25 mg/kg). Some mice that had been treated with 3-[[3-[[hydroxy[2-methoxy-3-(tetradecyloxy)phenoxy]-phosphinyl]oxy]phenyl]methyl]-5-methylthiazolium, hydroxide, inner salt followed by endotoxin were also treated intravenously with various doses of antiTNFα (doses ranging from 2.5 to 25 mg/kg). Two types of controls were included. One control consisted of mice that were treated with 3-[[3-[[hydroxy[2-methoxy-3-(tetradecyloxy)phenoxy]-phosphinyl]oxy]phenyl]methyl]-5-methyl-thiazolium, hydroxide, inner salt followed by endotoxin and saline (saline administered 1 hour post endotoxin treatment). Another control consisted of mice treated with saline followed by endotoxin and saline (saline administered 1 hour post endotoxin). The mice were monitored for 48 hours. The results of these experiments are shown in Table II.

Control mice that had been pretreated either with 3-[[3-[[hydroxy[2-methoxy-3-(tetradecyloxy)phenoxy]-phosphinyl]oxy]phenyl]methyl]-5-methylthiazolium, hydroxide, inner salt or saline followed by endotoxin died within 24 or 48 hours. All mice treated with saline followed by endotoxin and various doses of antiTNFα (antiTNFα administered 1 hour post endotoxin treatment) also died within 48 hours. The only survivors at 48 hours (five out of ten treated mice survived) belonged to the group that had been treated with 3-[[3-[[hydroxy[2-methoxy-3-(tetradecyloxy)phenoxy]-phosphinyl]oxy]phenyl]methyl]-5-methyl-thiazolium, hydroxide, inner salt followed by endotoxin and antiTNFα (25 mg/kg). These observations indicate that mammals can be pretreated in a prophylactic manner with a PAF antagonist followed by antiTNFα to prevent any potential endotoxin toxicity.

TABLE I

Combination Effect of 3-[[3-[[hydroxy[2-methoxy-3-(tetradecyloxy)phenoxy]-phosphinyl]oxy]phenyl]methyl]-5-methyl-thiazolium, hydroxide, inner salt (PAF antagonist)[1] and antiTNFα on Endotoxin Induced Lethality

| Treatment | Alive/Treated | | |
|---|---|---|---|
| | 24 hours | 48 hours | 72 hours |
| TDOPT (PAF antagonist) 20 mg/kg 20' after LPS | 0/5 | 0/5 | 0/5 |
| TDOPT (PAF antagonist) (20 mg/kg) + antiTNF (25 mg/kg) 20' after LPS | 5/5 | 5/5 | 5/5[2] |
| AntiTNF (25 mg/kg) 20' after LPS | 2/5 | 2/5 | 0/5 |
| PBS Control 20' after LPS | 0/5 | 0/5 | 0/5 |

Drug and antibody were given by i.v. route at indicated doses 15-20' after 50 mg/kg i.v. endotoxin in male Balb/c mice.
[1]3-[[3-[[hydroxy[2-methoxy-3-(tetradecyloxy)phenoxy]phosphinyl]oxy]phenyl]methyl]-5-methyl-thiazolium, hydroxide, inner salt (PAF antagonist) will be called TDOPT (PAF antagonist).
[2]Still 5/5 by day 12.

TABLE II

Prophylaxis Protocol: PAF Antagonist 3-[[3-[[hydroxy[2-methoxy-3-(tetradecyloxy)phenoxy]-phosphinyl]oxy]phenyl]methyl]-5-methyl-thiazolium, hydroxide, inner salt 20 mg/kg (iv) and anti-TNFα (iv)[1]

| TDOPT or PBS (iv) period | LPS (iv) | antiTNFα (iv) TDOPT (iv) | | observation | | |
|---|---|---|---|---|---|---|
| | | treatment | | HOURS live/treated | | |
| 0 hrs. | 2 hrs. | 3 hrs. | | 24 hrs. | 48 hrs. | 72 hrs. |
| PBS | LPS | PBS | | 0/20 | | |
| TDOPT | LPS | PBS | | 1/10 | 0/10 | |
| TDOPT | LPS | TDOPT | | 0/10 | | |
| PBS | LPS | antiTNFα | (500) | 0/10 | | |
| | | | (250) | 2/10 | 0/10 | |
| | | | (100) | 0/10 | | |
| | | | (50) | 0/10 | | |
| TDOPT | LPS | antiTNFα | (500) | 6/10 | 5/10 | 5/10 |
| | | | (250) | 3/10 | 0/10 | |
| | | | (100) | 4/10 | 0/10 | |
| | | | (50) | 2/10 | 0/10 | |

[1]The (PAF antagonist) will be called TDOPT (PAF antagonist) in the above table.

EXAMPLE 3

Preparation of Rabbit LPS (endotoxin) Antibody

E. coli LPS (endotoxin) was obtained from Sigma Chemical Co., St. Louis, Mo. New Zealand rabbits were challenged with 100 μg of LPS dissolved in PBS and mixed 1:1 with incomplete Freund's adjuvant (ICFA). Two weeks later, the rabbits were boosted with another 50 μg LPS/ICFA (1:1). Ten days later the rabbits were bled (approximately 40 ml/rabbit/month). The whole blood was maintained at 37° C. for 1 hour and then refrigerated overnight. The blood was centrifuged at 2000 rpm for 15 min. and the serum was collected.

A saturated solution of ammonium sulfate was added to the cold serum to bring the final concentration of ammonium sulfate up to 50%. The mixture was then stirred at 40° C. for 4 hours. The mixture was centrifuged at 10,000 rpm for 15 minutes. The liquid was decanted and the pellet was reconstituted with PBS to a final volume equal to the original volume of serum. This solution was then dialyzed against PBS for 48 hours. The resulting solution was filtered through a 40 micron filter. The resulting solution contains approximately 5 mg/ml rabbit IgG antibody.

As illustrated by the following example (Example 4), the combination of a PAF antagonist and an antibody directed against LPS (endotoxin) shows significantly better efficacy than the PAF antagonist or antibody used alone.

EXAMPLE 4

Balb/c mice (male, 20 g) were obtained from Charles River Laboratories, Wilmington, MA. They were housed in groups of 5 in individual cages and fed ad libitum. E. Coli endotoxin (LPS) was obtained from Sigma Chemical Co., St. Louis, Mo. The mice were first pretreated with a saline solution of the PAF antagonists 3-[[3-[[hydroxy[2-methoxy-3-(tetradecyloxy)phenoxy]-phosphinyl]oxy]phenyl]methyl]-5-methylthiazolium, hydroxide, inner salt, antagonist 1, or 3-[[3-[[hydroxy[2-methoxycarbonyl-3-(tetradecyloxy)phenoxyl]-phosphinyl'oxy]phenyl]methyl]-5-methyl-thiazolium, hydroxide, inner salt, antagonist 2, at doses at 40, 20, 10 and 5 mg/kg i.p. Two hours later the mice received an i.v. administration of endotoxin (LPS) dissolved in phosphate buffered saline at a dose at 50 mg/kg. One hour after endotoxin administration the mice received either the PAF antagonist alone at a dose of 40, 20, 10 or 5 mg/kg i.p., rabbit anti-LPS antibody alone at a dose of 0.4 ml/mouse i.v. (about 2 mg of IgE antibody), or a combination of the PAF antagonist at the same doses with the anti-LPS antibody also at the same dose. Four hours after endotoxin administration the mice again received the PAF antagonist. At 24 and 48 hours, the mice were treated with B.I.D. with the PAF antagonist at a dose at 40, 20, 10 or 5 mg/kg i.p.

A separate group of mice, which served as controls, received only endotoxin (LPS).

This protocol may be summarized in the following diagram:

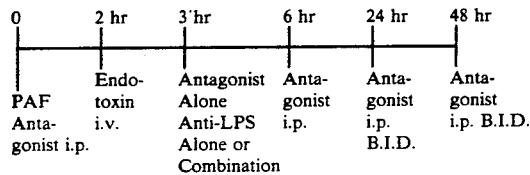

The results of this experiment are given hereinbelow in Table III

TABLE III

The Effect of Antagonist-1[1] or Antagonist-2[2] in Combination With Anti-LPS on Endotoxin-Induced Lethality in Mice

| Treatment (Dose mg/kg) | 24 Hrs (% Survival) | | 48 Hrs (% Survival) | |
|---|---|---|---|---|
| Antagonist-1 (40) | 0/23 | (0%) | 0/13 | (0%) |
| Antagonist-1 (20) | 3/35 | (9%) | 0/25 | (0%) |
| Antagonist-1 (10) | 6/34 | (18%) | 0/24 | (0%) |
| Antagonist-1 (5) | 0/10 | (0%) | 0/10 | (0%) |
| Antagonist-1 (40) + Anti-LPS | 3/24 | (13%) | 0/14 | (0%) |
| Antagonist-1 (20) + Anti-LPS | 17/32 | (53%) | 7/23 | (30%) |
| Antagonist-1 (10) + Anti-LPS | 23/33 | (70%) | 9/23 | (39%) |
| Antagonist-1 (5) + Anti-LPS | 4/8 | (50%) | 3/8 | (38%) |
| Antagonist-2 (40) | 2/24 | (8%) | 0/14 | (0%) |
| Antagonist-2 (20) | 6/34 | (18%) | 0/24 | (0%) |
| Antagonist-2 (10) | 8/34 | (24%) | 0/25 | (0%) |
| Antagonist-2 (5) | 2/10 | (20%) | 0/10 | (0%) |
| Antagonist-2 (40) + Anti-LPS | 8/23 | (35%) | 0/13 | (0%) |
| Antagonist-2 (20) + Anti-LPS | 19/34 | (56%) | 11/24 | (46%) |
| Antagonist-2 (10) + Anti-LPS | 22/34 | (65%) | 13/25 | (52%) |
| Antagonist-2 (5) + Anti-LPS | 3/10 | (30%) | 1/10 | (10%) |
| Anti-LPS Alone | 5/35 | (14%) | 0/25 | (0%) |
| LPS Controls | 0/40 | (0%) | 0/30 | (0%) |

[1] 3-[[3-[[hydroxy[2-methoxy-3-(tetradecyloxy)phenoxy]phosphinyl]oxy]phenyl]methyl]-5-methyl-thiazolium, hydroxide, inner salt
[2] 3-[[3-[[hydroxy[2-methoxycarbonyl-3-(tetradecyloxy)phenoxy]phosphinyl]oxy]phenyl]-methyl]-5-methyl-thiazolium, hydroxide, inner salt
As described above in Table III, all control mice receiving LPS (endotoxin) died. Mice treated with anti-LPS alone or PAF antagonists 1 or 2 alone were significantly less well protected aginst the lethal effects of endotoxin than mice treated with a combination of anti-LPS and antagonist-1 or antagonist-2. In fact, at 48 hours, only mice that received a combination therapy survived.

We claim:

1. A method of treating endotoxic shock in a mammal which comprises administering to the mammal a therapeutically effective amount of an antagonist to Platelet Activating Factor in combination with a therapeutically effective amount of one or more monoclonal or polyclonal antibodies directed towards either Tumor Necrosis Factor $\alpha$, Interleukin-1$\beta$, Gamma Interferon, or bacterial cell wall lipopolysaccharides.

2. A method according to claim 1, of treating endotoxic shock in a mammal wherein the monoclonal or polyclonal antibody is directed towards Tumor Necrosis Factor $\alpha$.

3. A method according to claim 2, of treating endotoxic shock in a mammal wherein the monoclonal or polyclonal antibody directed towards Tumor Necrosis Factor $\alpha$ is in combination with an antagonist of Platelet Activating Factor of the formula

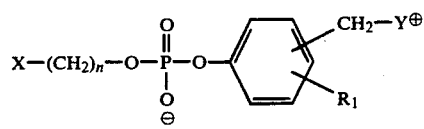

wherein:

X is a phenyl or naphthyl ring optionally substituted in any position with one or more substituents of:
   i) —$R_2$ wherein $R_2$ is $C_1$–$C_{25}$ alkyl, $C_1$–$C_{25}$ alkenyl, $C_1$–$C_{25}$ alkoxy, $C_1$–$C_{25}$ alkenyloxy, $C_1$–$C_{25}$ thioalkyl, phenyl, phenoxy, substituted phenyl or substituted phenoxy wherein the substituents are $C_1$–$C_{20}$ alkyl, $C_1$–$C_{20}$ alkoxy, halogen or trifluoromethyl;
   ii) hydrogen, halogen, trifluoromethyl, cyano or nitro;
   iii) —$CO_2R_3$, —$CONHR_3$, —CHO, $OCONHR_3$, or —$NHCOR_3$ wherein $R_3$ is $C_1$–$C_{25}$ alkyl, $C_1$–$C_{25}$ alkenyl, phenyl or substituted phenyl wherein the substituents are $C_1$–$C_{20}$ alkyl, $C_1$–$C_{20}$ alkoxy, halogen, or trifluoromethyl; $R_1$ is one or more substituents of the aromatic ring which may be in any position and is hydrogen, $C_1$–$C_5$ alkyl, $C_1$–$C_5$ alkoxy, or halogen; —$CH_2$—Y is a single substituent of the aromatic ring which may occupy any position wherein Y is a mono or bicyclic aromatic heterocycle with 5–7 membered rings containing at least one nitrogen atom which is bonded to the methylene group and optionally one or more other nitrogen or sulfur atoms.

4. A method according to claim 3 wherein Y of Formula I, is:

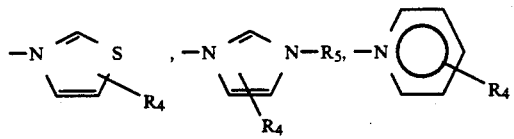

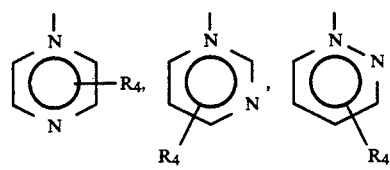

-continued

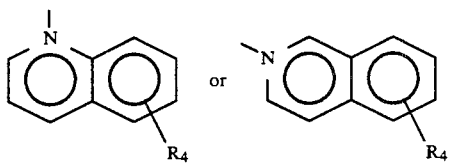

R4 is one or more substituents of the heterocyclic ring which may occupy a non-hetero atom position and is $C_1$-$C_5$ alkyl, $C_1$-$C_5$ alkoxy, hydrogen or halogen; $R_5$ is $C_1$-$C_5$ alkyl and hydrogen; and n is the integer 0 or 1.

5. A method according to claim 2, of treating endotoxic shock in a mammal wherein the monoclonal or polyclonal antibody directed towards Tumor Nacrosis Factor α is in combination with an antagonist of Platelet Activating Factor of the formula:

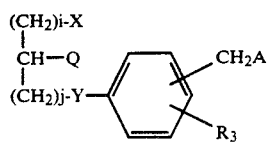

Formula II wherein:
(A) X is
  i) $C_1$-$C_{24}$ alkyl;
  ii) $C_1$-$C_{24}$ alkoxy;
  iii) $C_1$-$C_{24}$ carboamoyloxy;

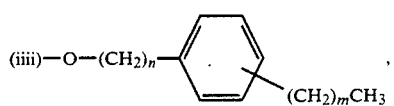

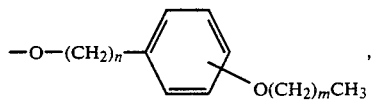

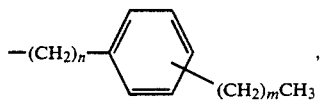

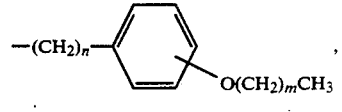

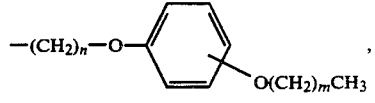

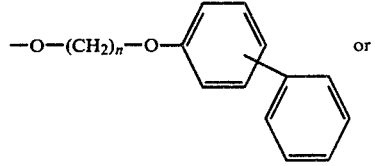

or

-continued

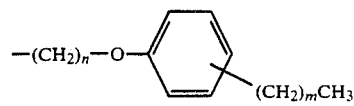

n is an integer from 1 to 25 and m is an integer from 0 to 24 and the sum of n and m is less than or equal to 25;
v) phenyl;
vi) mono- or polysubstituted phenyl substituted with $C_1$-$C_{20}$ alkyl, $C_1$-$C_{20}$ alkoxy, halogen, trifluoromethyl, phenyl, substituted phenyl or benzyloxy;
vii) phenoxy;
viii) mono- or polysubstituted phenoxy substituted with $C_1$-$C_{20}$ alkyl, $C_1$-$C_{20}$ alkoxy, halogen, trifluoromethyl, phenyl, substituted phenyl or benzyloxy;
ix) naphthaloxy;
x) mono- or polysubstituted naphthaloxy substituted with $C_1$-$C_{20}$ alkyl, $C_1$-$C_{20}$ alkoxy or halogen;
xi) —O—$(CH_2)_r$—O—$((CH_2)_pO)_t$—$(CH_2)_a$—W wherein W is methyl or phenyl optionally substituted with $C_1$-$C_3$ alkyl, $C_1$-$C_3$ alkoxy or phenyl, r, p, t and a are integers such that the expression r+(p+1)t+a is also an integer and has a value of 3 to 20; r is greater than or equal to 2; p is greater than or equal to 2; t is greater than or equal to zero; and a is greater than or equal to zero;
(B) i is an integer from 1 to 3 and j is an integer from 1 to 6;
(C) Q is —OR₂,

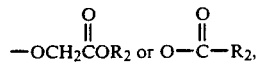

wherein $R_2$ is hydrogen, $C_1$-$C_6$ alkyl or $C_1$-$C_6$ alkenyl;
(D) Y is a divalent radical

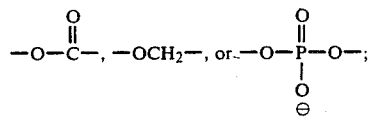

(E) $R_3$ is one or more $C_1$-$C_5$ alkyl, $C_1$-$C_5$ alkoxy or halogen substituents of the aromatic ring;
(F) —CH₂A may be in the ortho, meta or para position wherein A is
  a mono or bicyclic aromatic heterocycle with 5-7 membered rings containing at least one nitrogen atom which is bonded to the methylene group and optionally one or more other nitrogen or sulfur atoms.

6. A method according to claim 5 wherein A of Formula II is:

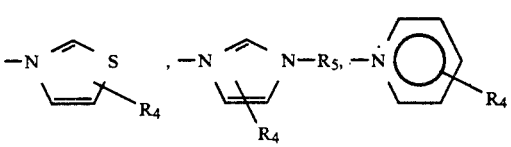

-continued

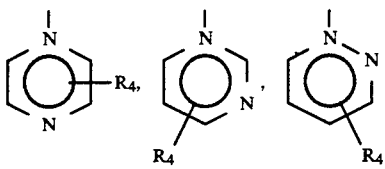

-continued

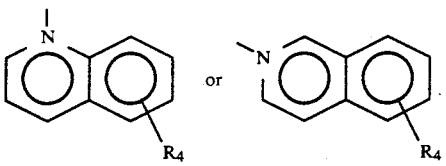

wherein $R_4$ is one or more substituents of the heterocyclic ring which may occupy a non-hetero atom position and is $C_1$–$C_5$ alkyl, $C_1$–$C_5$ alkoxy, hydrogen or halogen; $R_5$ is $C_1$–$C_5$ alkyl and hydrogen; and the configuration at the asymmetric carbon atom is R, S, or racemic.

7. A composition comprising a therapeutic combination of an antagonist to Platelet Activating Factor and one or more monoclonal or polyclonal antibodies.

* * * * *